(12) United States Patent
Itou et al.

(10) Patent No.: US 8,523,841 B2
(45) Date of Patent: Sep. 3, 2013

(54) CATHETER WITH SPIRAL SLIT TERMINATING IN SLIT TERMINATION PORTION ORIENTED TO SUPPRESS CRACK OCCURRENCE

(75) Inventors: Youichi Itou, Fujinomiya (JP); Yasunori Yamashita, Fujinomiya (JP); Youichirou Kuwano, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 172 days.

(21) Appl. No.: 13/040,356

(22) Filed: Mar. 4, 2011

(65) Prior Publication Data

US 2011/0224650 A1 Sep. 15, 2011

(30) Foreign Application Priority Data

Mar. 12, 2010 (JP) ................................ 2010-055795

(51) Int. Cl.
*A61M 25/00* (2006.01)
*A61B 8/00* (2006.01)

(52) U.S. Cl.
USPC .......................................... 604/525; 600/439

(58) Field of Classification Search
USPC ................. 604/437, 439, 459, 462, 525, 524; 600/525, 437, 439, 459, 462
See application file for complete search history.

(56) References Cited

U.S. PATENT DOCUMENTS

| | | | | |
|---|---|---|---|---|
| 4,899,787 A | * | 2/1990 | Ouchi et al. | 138/131 |
| 4,917,666 A | * | 4/1990 | Solar et al. | 604/95.01 |
| 4,960,410 A | * | 10/1990 | Pinchuk | 604/96.01 |
| 5,125,895 A | * | 6/1992 | Buchbinder et al. | 604/95.01 |
| 5,180,376 A | * | 1/1993 | Fischell | 604/524 |
| 5,531,719 A | * | 7/1996 | Takahashi | 604/525 |
| 5,569,200 A | * | 10/1996 | Umeno et al. | 604/102.02 |
| 5,599,326 A | * | 2/1997 | Carter | 604/524 |
| 5,741,429 A | * | 4/1998 | Donadio et al. | 216/8 |
| 5,827,231 A | * | 10/1998 | Harada | 606/194 |
| 5,876,331 A | * | 3/1999 | Wu et al. | 600/139 |

(Continued)

FOREIGN PATENT DOCUMENTS

EP 0 688 576 A1 12/1995
EP 0 761 253 A2 3/1997

(Continued)

OTHER PUBLICATIONS

Extended European Search Report issued on Jun. 14, 2011 by the European Patent Office in corresponding European Patent Application No. 11 15 6940.

*Primary Examiner* — Kevin C Sirmons
*Assistant Examiner* — William Carpenter
(74) *Attorney, Agent, or Firm* — Buchanan Ingersoll & Rooney PC

(57) ABSTRACT

A catheter comprising a sheath to be inserted into a living body, wherein the sheath includes a tubular reinforcement layer of at least one layer, which is formed with a spiral slit continuous from the distal side to the proximal side thereof; a termination end of the spiral slit is provided on the proximal side of the slit proximal portion at the site of the proximal side of the spiral slit; and at the same time, there is formed a slit termination portion in which inclination angle of the spiral slit with respect to the circumferential direction of the reinforcement layer is larger than that of the slit proximal portion.

20 Claims, 12 Drawing Sheets

(56) References Cited

U.S. PATENT DOCUMENTS

| | | | |
|---|---|---|---|
| 6,048,338 A * | 4/2000 | Larson et al. | 604/523 |
| 7,968,038 B2 * | 6/2011 | Dittman et al. | 264/342 R |
| 8,105,311 B2 * | 1/2012 | Schneider et al. | 604/523 |
| 2004/0064024 A1 * | 4/2004 | Sommer | 600/374 |
| 2004/0116850 A1 | 6/2004 | Schneider et al. | |
| 2006/0100571 A1 * | 5/2006 | Venturelli | 604/43 |
| 2007/0088257 A1 * | 4/2007 | Fisher et al. | 604/103.04 |
| 2009/0247878 A1 * | 10/2009 | Tanioka et al. | 600/462 |

FOREIGN PATENT DOCUMENTS

| | | |
|---|---|---|
| EP | 1 428 545 A1 | 6/2004 |
| JP | 2009-240710 A | 10/2009 |
| WO | WO 2004/047899 A1 | 6/2004 |

\* cited by examiner

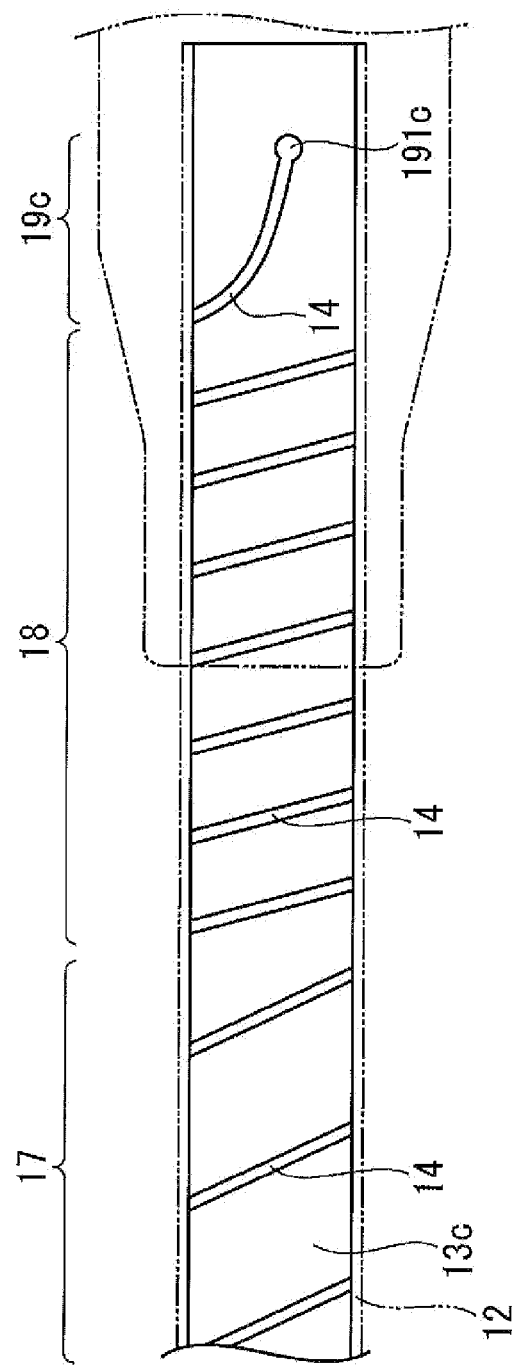

CATHETER WITH SPIRAL SLIT TERMINATING IN SLIT TERMINATION PORTION ORIENTED TO SUPPRESS CRACK OCCURRENCE

This application claims priority to Japanese Patent Application No. 2010 055795 filed on Mar. 12, 2010, the entire content of which is incorporated herein by reference.

FIELD OF THE INVENTION

The present invention generally pertains to a catheter. More specifically, the invention relates to a catheter insertable into a living body such as a blood vessel, a vascular channel and the like.

BACKGROUND DISCUSSION

Imaging diagnosis which have been performed in the past involve inserting an ultra-sound catheter having an imaging function into, for example, a blood vessel of a cardiac coronary artery or into a vascular channel of a bile duct.

The imaging diagnostic apparatus can be an intra vascular ultra-sound diagnostic apparatus (Intra Vascular Ultra Sound: IVUS). Generally, an intra vascular ultra-sound diagnostic apparatus includes a probe, installed with an ultrasonic transducer, that is scanned radially in the inside of a blood vessel. A reflection wave (ultra-sound echo) reflected by biological tissue of a lumen (e.g., blood vessel lumen) is received by the same ultrasonic transducer, and thereafter, a process of amplification, detection or the like is applied and a cross-sectional image of a blood vessel is created based on the strength of the produced ultra-sound echo.

An optical coherence tomography diagnostic apparatus (Optical Coherence Tomography: OCT) has also been utilized as the imaging diagnostic apparatus. The optical coherent tomography diagnostic apparatus is an apparatus in which a probe, installed with an optical fiber attached to a probe provided with an optical lens and an optical minor at its distal end, is inserted into the inside of a blood vessel, light is illuminated in the blood vessel while radially scanning the optical minor which is arranged on the distal side of the optical fiber and a cross-sectional image of the blood vessel is created based on reflection light from biological tissue.

There has relatively recently been proposed an imaging diagnostic apparatus using an optical frequency domain imaging method (Optical Frequency Domain Imaging: OFDI) which is evaluated as a next-generation OCT.

Japanese Unexamined Patent Application Publication No. 2009-240710 describes a probe for insertion into a living body, forming part of an intra vascular ultra-sound diagnostic apparatus. This probe for insertion into a living body is provided with a metal tube formed with a spiral slit as a reinforcement layer in a sheath inserted into the living body.

The probe for insertion into a living body which is used for the OCT or the OFDI includes a sheath and a shaft for data acquisition. An image is obtained by rotating the shaft for data acquisition at relatively high speed in the sheath and is moved to the proximal side while being rotated. When inserting the probe into a guiding catheter, it sometimes happens that a kink occurs at a proximal portion of the sheath. In particular, when rigidity at the proximal portion of the sheath becomes too high, steerability decreases during insertion into the guiding catheter and it becomes relatively easy for a kink to occur.

Consequently, with respect to the probe for insertion into a living body described in Japanese Unexamined Patent Application Publication No. 2009-240710, steerability is improved by increasing the flexibility on the distal side of the probe which is accomplished by increasing the slit density on the distal side of the reinforcement layer (total surface area of slit portion which exists for a predetermined unit length in the axial direction of the reinforcement layer) as compared to the slit density of the center portion. The occurrence of kinking is reduced, yet the proximal portion of the sheath exhibits steerability, by imparting a certain degree of flexibility to the proximal portion by virtue of the slit density on the proximal side of the reinforcement layer being less than the slit density of the center portion.

When the density of the slit at the proximal side is increased compared with the slit density of the center portion of the reinforcement layer in the manner described in Japanese Unexamined Patent Application Publication No. 2009-240710, rigidity decreases on the proximal side of the reinforcement layer, and there is a possibility that a crack will occur at the termination end on the proximal side of the slit.

SUMMARY

According to one aspect disclosed here, a catheter includes a sheath sized for insertion into a living body and having a tubular reinforcement layer comprised of at least one layer, with the tubular reinforcement layer including a spiral slit extending continuously from a distal side of the tubular reinforcement layer to a proximal side of the tubular reinforcement layer. A termination end of the spiral slit is located at a proximal side of a proximal slit portion of the tubular reinforcement layer, and the slit is located in the proximal slit portion of the tubular reinforcement layer. The tubular reinforcement layer also comprises a slit termination portion in which a proximal portion of the slit, including the termination end, is located. The slit in the slit termination portion and the slit in the other slit portion extend at an inclination angle relative to a circumferential direction of the intermediate tube, and the inclination angle of the slit in the slit termination portion is larger than the inclination angle of the slit in the proximal slit portion.

The catheter can also include, on the proximal side of the slit proximal portion, a slit termination portion in which inclination angle with respect to the circumferential direction of the reinforcement layer is larger than that of the slit proximal portion to improve rigidity of the sheath depending on the slit termination portion whose inclination angle is relatively large and to improve security by suppressing occurrence of a crack at the termination end of the slit.

The slit termination portion can be constructed such that the inclination angle changes gradually from the slit proximal portion, and so the rigidity of the reinforcement layer changes relatively smoothly and stress concentration is suppressed in which occurrence of a crack can be more reliably repressed.

Employing an inclination angle of 90 degrees or less makes it difficult for the force in the direction of being opened to act when a tensile force or a bending moment acts on the sheath and so the occurrence of a crack can be repressed.

The spiral slit can include, on the distal side of the slit proximal portion, a slit intermediate portion whose slit density is relatively low compared with that of the slit proximal portion, and can also include, on the distal side away from the slit intermediate portion, a slit distal portion whose slit density is relatively high compared with that of the slit intermediate portion. This provides flexibility at the distal portion of the sheath as well as on the proximal side, and improves steerability of the distal side. This also reduces the occurrence of kinking while securing steerability at the proximal portion of the sheath.

The site corresponding to the slit termination portion of the sheath can be covered by a kink repression member shrinking in its diameter toward the distal side, so that the occurrence of kinking of the sheath is more reliably suppressed as well as the occurrence of a crack at the termination end of the slit.

The catheter disclosed here inhibits the occurrence of a crack at the termination end of the slit of the reinforcement layer which is provided in the sheath is repressed and security can be improved.

According to another aspect, a catheter comprises a sheath sized to be inserted into a living body, and including two coaxial tubes each possessing a lumen open at opposite end portions of the respective tube, and the inner surface of one tube being in contact with the outer surface of the other tube, and wherein the two tubes comprise a first tube and a second tube. The first tube includes a spiral slit extending continuously from a distal side of the first tube to a proximal side of the first tube, and extending completely radially through first tube. The first tube including plural slit portions in which the slit is located, the slit in each slit portion extending completely around the circumference of the first tube plural times, and one of the plural slit portions possessing a slit density different from the slit density of the slit in an other of the slit portions, with the other slit portion being positioned proximally of the one slit portion. The first tube comprises a slit termination portion in which a proximal end portion of the spiral slit is located. The slit terminates at a terminating end located in the slit termination portion of the first tube, the slit termination portion being positioned proximally of the other slit portion. The slit in the slit termination portion and the slit in the other slit portion extending at an inclination angle relative to a circumferential direction of the intermediate tube, with the inclination angle of the slit in the slit termination portion being larger than the inclination angle of the slit in the other slit portion.

In accordance with a further aspect, a catheter comprises a sheath sized to allow the sheath to be inserted into a living body, and including an inside tube, an intermediate tube and an outside tube. The inside tube, the intermediate tube and the outside tube are coaxially arranged and each possesses a lumen open at opposite end portions of the respective tube. The inside tube, the intermediate tube and the outside tube each possess an inner surface and an outer surface, with the inner surface of the outer tube being in contact with the outer surface of the intermediate tube, and the inner surface of the intermediate tube being in contact with the outer surface of the inner tube. The intermediate tube includes a spiral slit extending continuously from the distal side of the intermediate tube to the proximal side of the intermediate tube, with the slit extending radially completely through the intermediate tube to communicate the inner surface of the intermediate tube with the outer surface of the intermediate tube. The intermediate tube comprises a first slit portion in which the slit is located, a second slit portion in which the slit is located and a third slit portion in which the slit is located, the slit in the first slit portion possessing a slit density greater than the slit density of the slit in the second slit portion, and the slit in the third slit portion possessing a slit density greater than the slit density of the slit in the second portion, and wherein the second slit portion is positioned axially between the first slit portion and the third slit portion, and the first slit portion is positioned distally of the third slit portion. The first slit portion and the third slit portion possess different slit densities. The intermediate tube comprises a slit termination portion in which is located a terminating portion of the slit at a proximal end portion of the slit, and the slit termination portion is positioned proximally of the third slit portion. The spiral slit possesses a termination end at which the proximal-most end of the slit terminates, and the termination end is located in the slit termination portion of the intermediate tube. The slit in the slit termination portion and the slit in the third slit portion extend at an inclination angle relative to a circumferential direction of the intermediate tube, and the inclination angle of the slit in the slit termination portion is larger than the inclination angle of the slit in the third slit portion.

BRIEF DESCRIPTION OF THE DRAWINGS

FIG. 12 is a plan view of still another example of the proximal portion of the sheath main body.

DETAILED DESCRIPTION

Figure 1:
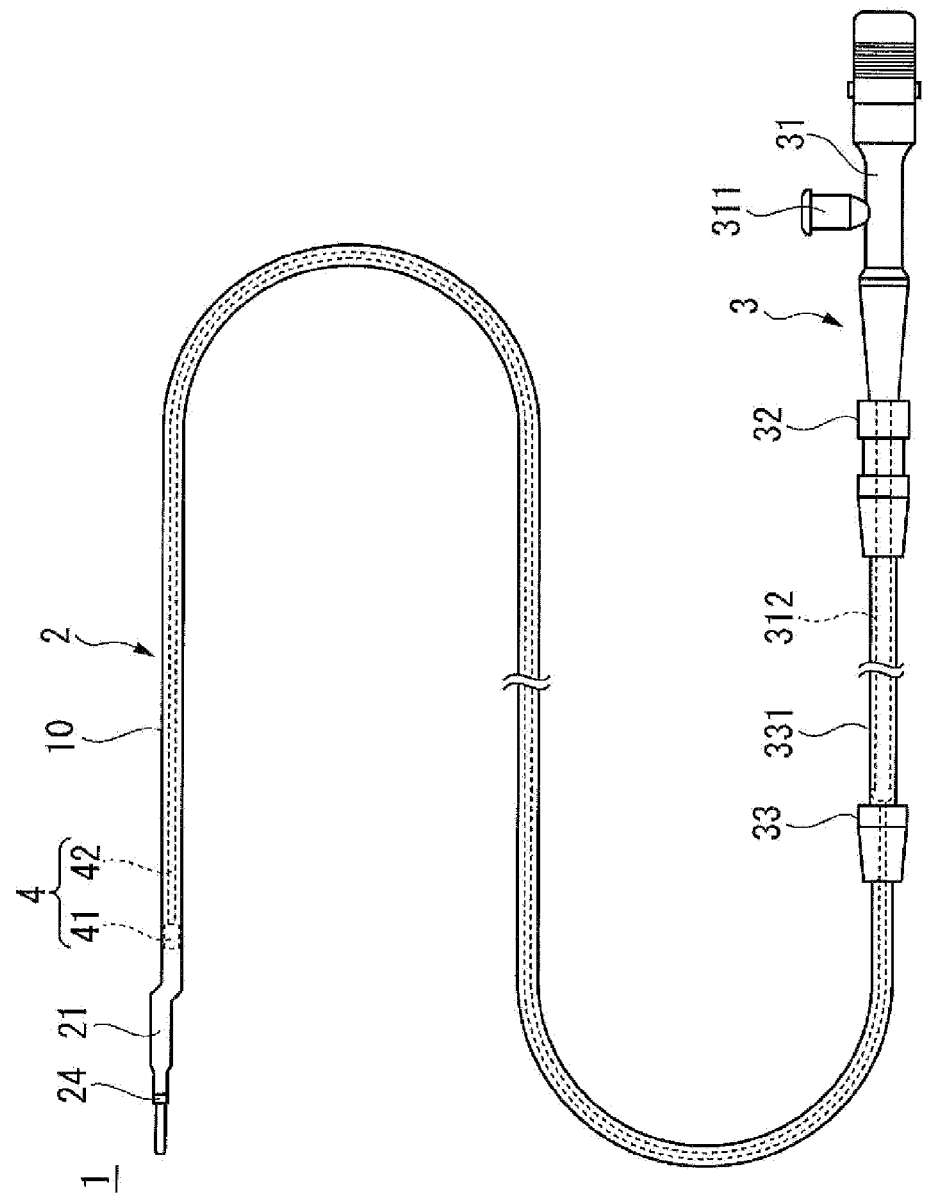
FIG. 1 is a plan view of an ultra-sound catheter according to one disclosed embodiment.

Set forth below is a description of embodiments of the catheter disclosed here. For purposes of convenience and ease in illustration, the size ratio of various parts and features of the catheter illustrated in the drawing figures is exaggerated and is not intended to be an accurate representation of the actual relative sizes.

The catheter described below by way of example is an ultra-sound catheter 1 for observing the inside of a body cavity or lumen (e.g., the inside of a blood vessel) by ultrasonic diagnosis.

The ultra-sound catheter 1, as shown in FIG. 1, includes a sheath 2 sized for insertion into a body cavity, an imaging core 4 for transmitting and receiving ultra-sound with respect to a tissue in the body cavity, and a steering unit 3 through which the imaging core 4 passes. The steering unit 3 is positioned on the proximal side from the sheath 2.

Figure 2:
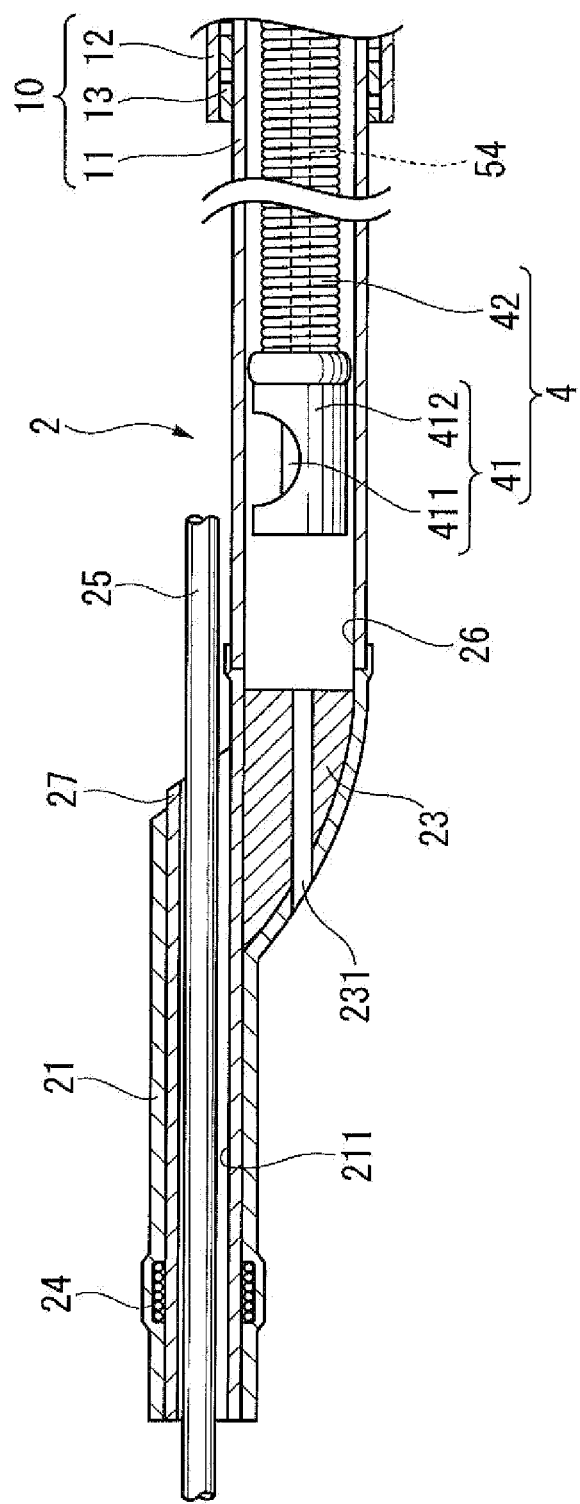
FIG. 2 is a longitudinal cross-sectional view of a distal portion of the ultra-sound catheter.

The sheath 2, as shown in FIG. 2, includes a sheath distal portion 21, a sheath tube 10 and a filling liquid in/out-path member 23.

The sheath distal portion 21 includes a tubular sheath distal member 27 through which extends a through hole forming a guide wire lumen 211. An X-ray imaging marker 24 is positioned proximal of the distal end of the sheath distal portion 21 and distal of the filling liquid in/out-path member 23. During use, a guide wire 25 is inserted into the body cavity or lumen beforehand and while moving the sheath so that this guide wire 25 is passed through the guide wire lumen 211, the ultra-sound catheter 1 is introduced to a target lesion. The X-ray imaging marker 24 allows the distal position of the ultra-sound catheter 1 to be visually confirmed under X-ray illumination during insertion into the body cavity.

The filling liquid in/out-path member 23 includes a priming lumen 231 which is a hole, in communication with a lumen 26 inside the sheath tube 10, allowing a physiological salt solution introduced into the sheath tube 10 to flow to the outside.

The imaging core 4 is slidably installed in the sheath 2 in an axial direction of the sheath 2. This imaging core 4 includes a transducer unit 41 for transmitting and receiving the ultra-sound toward a tissue inside the body cavity, and a drive shaft 42 having a distal end attached to this transducer unit 41 which concurrently rotates the transducer unit. The transducer unit 41 is constituted by an ultrasonic transducer 411 (signal transmission & receiving member) for transmitting and receiving the ultra-sound and a housing 412 for housing the ultrasonic transducer 411.

The sheath tube 10 is formed of a material having a relatively high ultra-sound permeability. A site within an area in which the ultrasonic transducer 411 of the sheath 2 moves constitutes an acoustic window portion through which the ultra-sound is transmitted. The ultra-sound has a property of being reflected at a boundary portion at which acoustic impedance changes. During a diagnosis, more specifically while indwelling the ultra-sound catheter 1 in a blood vessel, the surrounding area of the ultra-sound catheter 1 is filled with blood (body liquid). Therefore, it is necessary for the catheter to be constituted such that a substance other than a substance having an equivalent acoustic impedance as that of the blood does not exist between the ultrasonic transducer 411 and the blood vessel wall which is a diagnosis target. The acoustic impedance is a constant specific or peculiar to a material, and is expressed as a product of the acoustic speed in the material (speed of sound) and density of the material. In an intraluminal side of the sheath 2, there is injected, as an ultra-sound transmission liquid, with a physiological salt solution whose acoustic impedance approximately coincides with that of the blood. Therefore, it is also necessary for the material constituting the sheath 2 to be a material having an equivalent acoustic impedance.

The drive shaft 42 has a characteristic of being flexible and also permits a rotational motion power produced in the steering unit 3 (see FIG. 1) to be transmitted to the transducer unit 41. By way of example, the drive shaft 42 is constituted by a tube body of a multi-layer coil shape such as a three-layer coil whose winding direction is alternated in a manner from right to left and again right. Owing to a fact that the drive shaft 42 transmits the rotational motion power, the transducer unit 41 rotates and it is possible to observe 360 degrees of the target lesion inside a body cavity such as a blood vessel, a vascular channel and the like. Also, with respect to the drive shaft 42, there is passed through, in the inside thereof, with a signal line 54 for transmitting a signal detected by the transducer unit 41 to the steering unit 3.

The steering unit 3 includes, as shown in FIG. 1, a hub 31 having a port 311 for injecting physiological salt solution for removing air, an unit connector 32 connected with the hub 31 through an inner tube 312 and a relay connector 33 which is connected to the unit connector 32 through the outer tube 331 and concurrently, which connects the sheath 2 and the steering unit 3.

The hub 31 holds the drive shaft 42 and the inner tube 312. By pressing the inner tube 312 into the unit connector 32 and the outer tube 331 or by pulling it out therein, the drive shaft 42 slides inside the sheath 2 in the axial direction.

When the inner tube 312 is pressed maximally, as shown in FIG. 1, with respect to the inner tube 312, an end portion thereof on the sheath side reaches until the vicinity of a sheath side end portion of the outer tube 331, more specifically, until the vicinity of the relay connector 33. Then, in this state, the transducer unit 41 is positioned at the vicinity of the distal end of the sheath tube 10 of the sheath 2.

Figure 3:
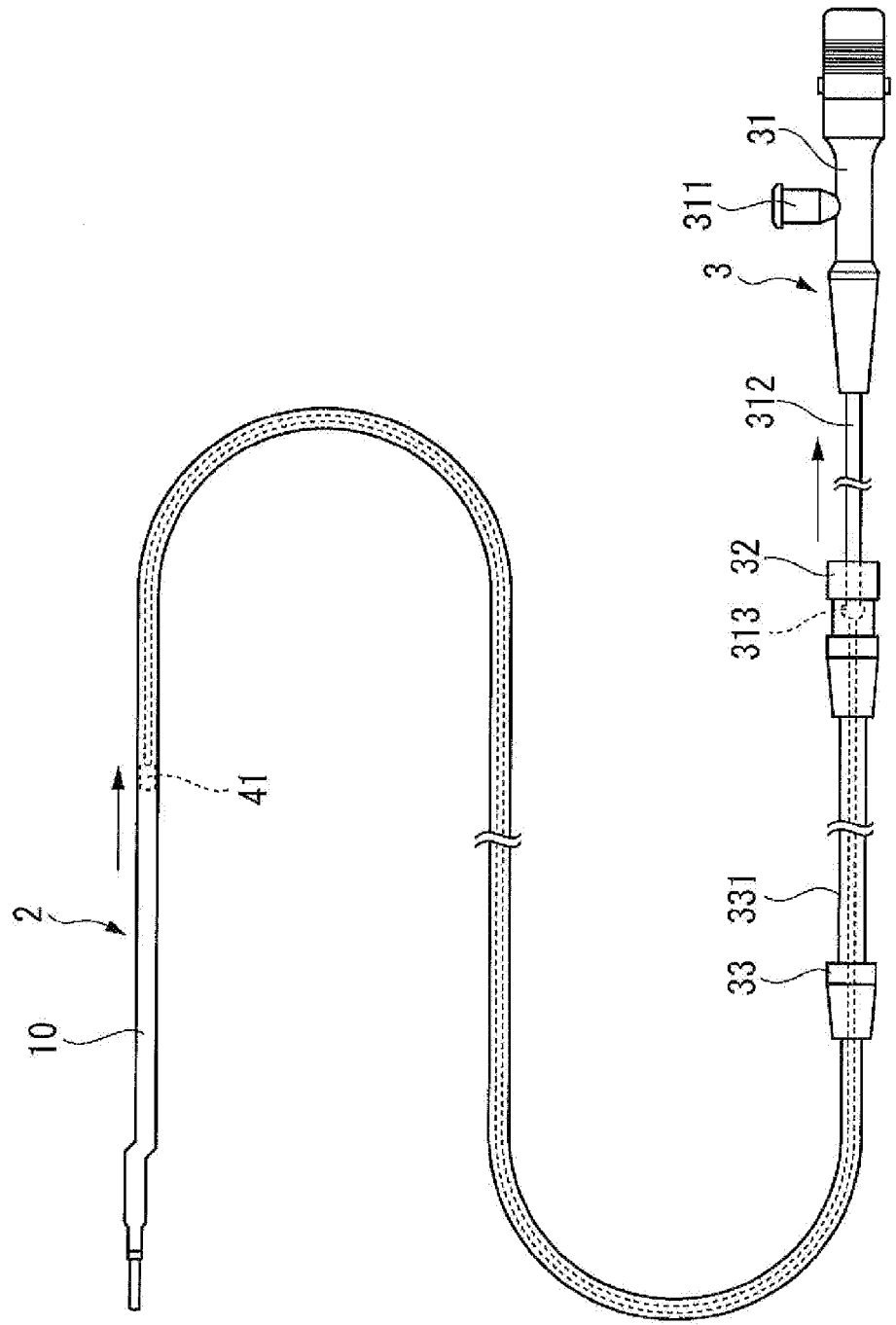
FIG. 3 is a plan view of the ultra-sound catheter when pulling back the transducer unit.

Also, when the inner tube 312 is pulled-out maximally, as shown in FIG. 3, with respect to the inner tube 312, a stopper 313 formed at the distal end thereof is engaged with the inner wall of the unit connector 32 and other than the portion which is engaged in the vicinity of the distal end will be exposed. Then, in this state, the transducer unit 41 is pulled back while remaining the sheath 2 in the inside thereof. Owing to a fact that the transducer unit 41 moves while being rotated, it is possible to create a tomographic image of such as a blood vessel, a vascular channel and the like.

Figure 4:
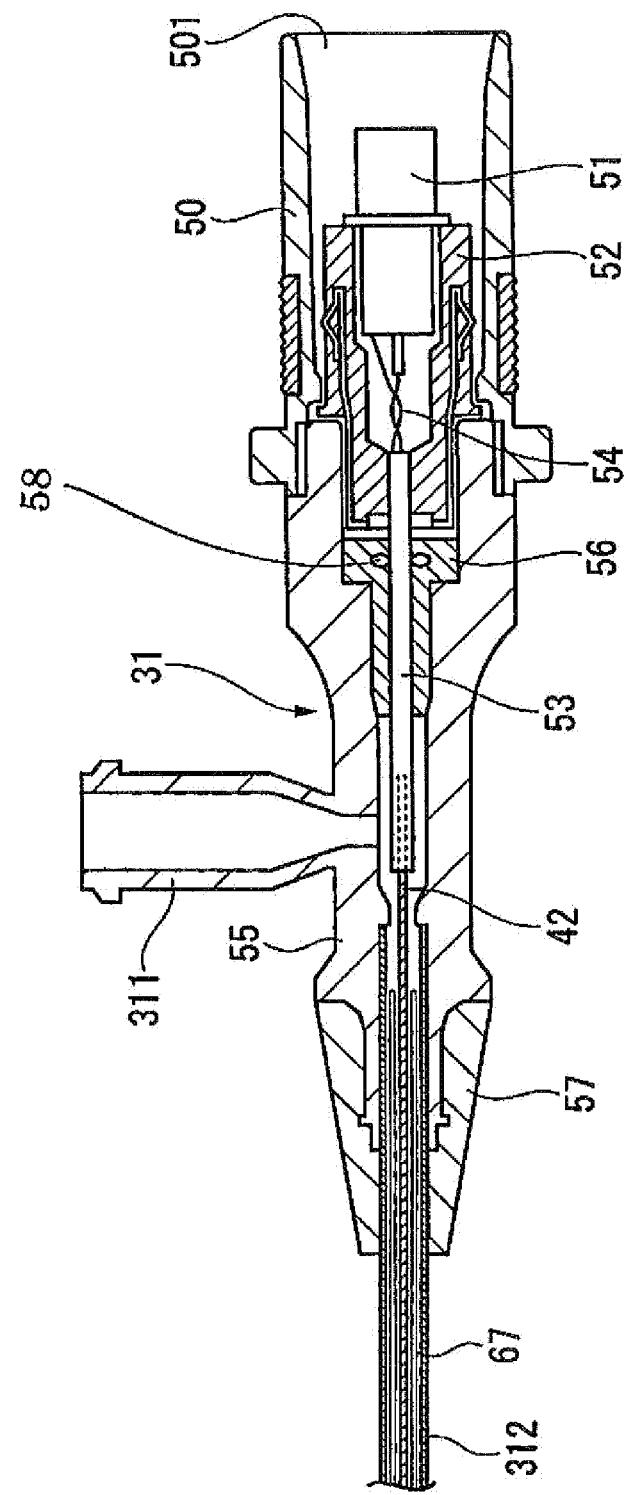
FIG. 4 is a longitudinal cross-sectional view of a hub of the ultra-sound catheter.

The hub 31 of the steering unit 3 includes, as shown in FIG. 4, a joint 50, a male connector 51, a rotor 52, a connection pipe 53, a signal line 54, a hub main body 55, a seal member 56 and an anti-kink protector 57.

The joint 50 includes an opening portion 501 on the proximal end or proximal side of the ultra-sound catheter 1, and inside the joint are positioned the male connector 51 and the rotor 52. The male connector 51 is interlinkable from the opening portion 501 side of the joint 50 to a female connector 711 forming part of an external drive apparatus 7 (see FIG. 11) so that the external drive apparatus 7 and the male connector 51 are interlinked mechanically and electrically.

The rotor 52 holds the connection pipe 53 against rotation (i.e., so that the connection pipe 53 is not rotatable relative to the rotor 52) and rotates integrally as one unit with the male connector 51. The end of the connection pipe 53 opposite to the rotor 52 holds the drive shaft 42 to transmit rotation of the rotor 52 to the drive shaft 42. The signal line 54 passes through the inside of the connection pipe 53. One end of the signal line 54 is connected to the male connector 51, and the other end passes through the inside of the drive shaft 42 and is connected to the transducer unit 41. An observation result in the transducer unit 41 is transmitted to the external drive apparatus 7 through the male connector 51, is appropriately processed, and is displayed as an image.

Physiological salt solution is injected into the port 311 of the hub main body 55 and is introduced into the inner tube 312 without leakage to the outside. The seal member 56 is installed together with an O-ring 58 between the hub main body 55 and the joint 50, so that the physiological salt solution does not leak out to the opening portion 501 side of the joint 50.

With respect to the hub main body 55, a portion of the inner tube 312 is fit together by insertion and the anti-kink protector 57 is arranged in surrounding relation to the inner tube 312 and the hub main body 55.

Figure 5:
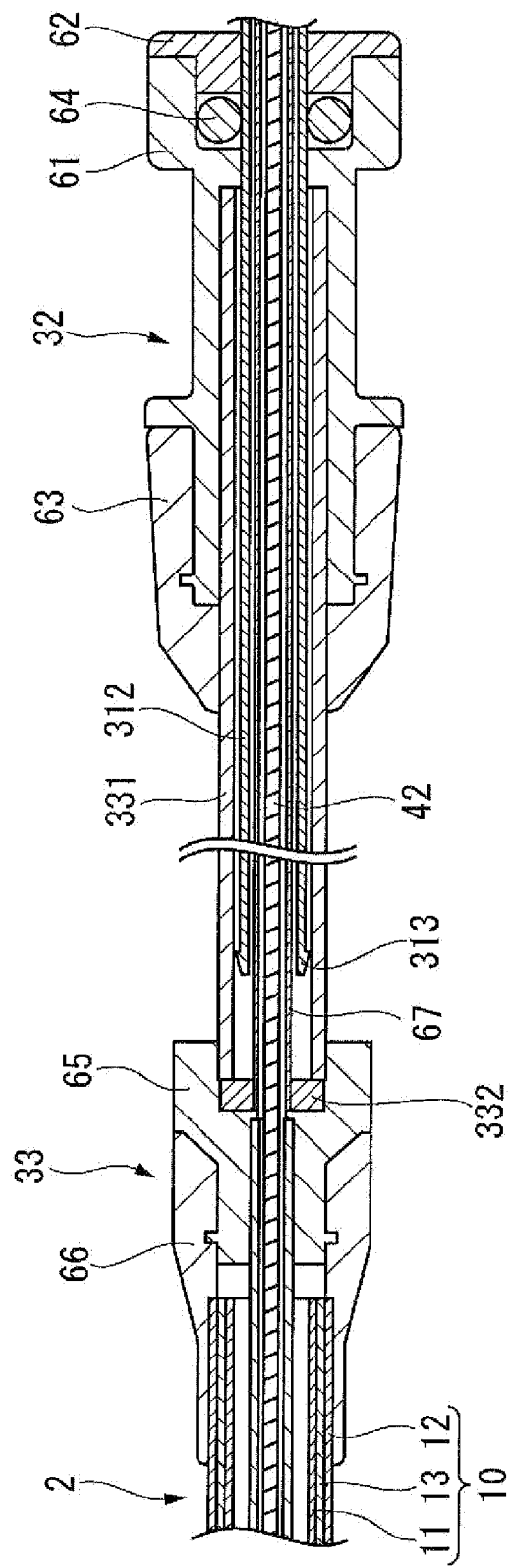
FIG. 5 is a longitudinal cross-sectional view of a unit connector and a relay connector of the ultra-sound catheter.

The unit connector 32 includes, as shown in FIG. 5, a unit connector main body 61, a sealing member 62, a cover member 63 and a packing 64.

The unit connector main body 61 is inserted with the outer tube 331 attached to the relay connector 33, and the inner tube 312 extended from the hub 31 is inserted in the inside of this outer tube 331. The sealing member 62 holds the packing 64 in combination with the unit connector main body 61, and the cover member 63 holds the outer tube 331 in combination with the unit connector main body 61. The packing 64 is sealed between the unit connector main body 61 and the sealing member 62, so that even if the physiological salt solution supplied to the port 311 of the hub 31 flows into the outer tube 331 through the inner tube 312, it does not leak to the outside of the unit connector 32.

The inner tube 312 extending from the hub 31 includes a stopper 313 at the distal end of the inner tube 312 so that when pulling the hub 31 to a maximum extent, more specifically even when pulling-out the inner tube 312 from the outer tube 331 the maximum amount, the stopper 313 does not engage with the inner wall of the unit connector main body 61, whereby the inner tube 312 is inhibited pr prevented (i.e., will not be pulled out) from the unit connector 32.

The relay connector 33 includes an outer tube hold portion 65 and an anti-kink protector 66. The outer tube hold portion 65 holds the outer tube 331. Also, the proximal end portion of the sheath 2 is interlinked with the inner face of the distal end portion of the outer tube hold portion 65. A path exists in the relay connector 33 for introducing the drive shaft 42 passing through from the outer tube 331 and the physiological salt solution into the sheath 2. By inserting a plurality of tubes further into the inside of this path, it is also possible to, for example, inhibit or prevent buckling of the drive shaft 42 and leakage of the physiological salt solution.

A protection tube 67 is fixed on the inner wall of an exit member 332 through which the drive shaft 42 of the outer tube hold portion 65 passes. This protection tube 67 extends toward the inside of the inner tube 312 extending from the hub 31 and is arranged between the drive shaft 42 and the inner tube 312. In the illustrated embodiment, the proximal end of the protection tube 67 terminates inside the hub main body 55 as shown in FIG. 4. When the outer tube 331 is pressed radially into the inner tube 312, the protection tube 67 is pressed into the inner tube 312 (resists the inward pressing) in a direction opposite to the direction of the pressing. When the inner tube 312 is pressed or pulled-out with respect to the outer tube 331, it happens that also the protection tube 67 is relatively pressed or pulled-out with respect to the inner tube 312 from the opposite direction, so that even if friction occurs by the contact with the inner tube 312 and a bending force occurs at the drive shaft 42, the bending force is repressed by the protection tube 67, and it is possible to prevent a bending or the like. It should be noted that the protection tube 67 is formed by a loosely wound coil shaped metal tube body and consequently, the physiological salt solution can flow into or out of gaps between adjacent windings in the coil and so air does not remain in the outer tube 331.

Figure 6:
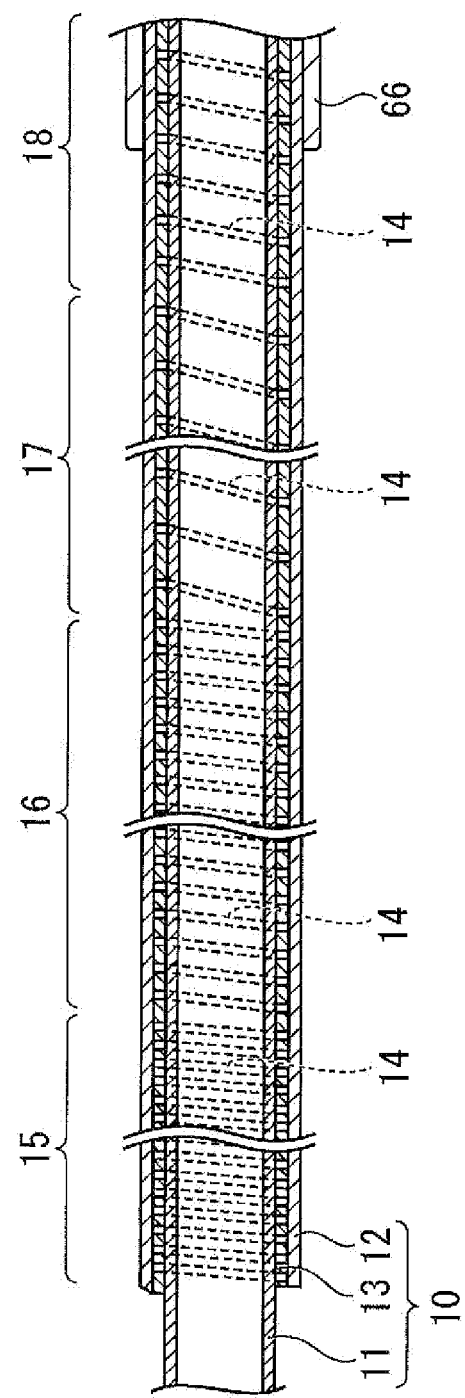
FIG. 6 is a longitudinal cross-sectional view of a sheath main body.

The sheath tube 10 of the ultra-sound catheter 1 is, as shown in FIG. 6, comprised of three coaxially arranged tubes, an inside tube 11, an intermediate tube 13 (reinforcement layer) and an outside tube 12. The sheath tube 10 is not limited only to a tube having such a three layer structure as it is also possible to employ a two layer structure tube or a tube composed of four layers or more.

The inside tube 11 is a tube body having the lumen 26 which extends from the proximal end to the distal end. The intermediate tube 13 is closely-attached to the outer surface of the inside tube 11. The outside tube 12 is closely-attached to the outer surface of the intermediate tube 13 (i.e., the inner surface of the intermediate tube 13 contacts the outer surface of the inner tube 11). The thickness of the inside tube 11 is 30 µm to 300 µm and preferably has a tensile breaking strength of at least 0.4 Kgf or more.

The distal end of the inside tube 11 extends distally beyond the distal ends of the intermediate tube 13 and the outside tube 12 by a predetermined length, and so the distal portion of the sheath tube 10 is constituted only by the inside tube 11. It is preferable for the distance between the distal ends of the intermediate tube 13 and the outside tube 12 and the distal end of the inside tube 11 to be around 100 mm to 250 mm. It is preferable for the outer diameter of the sheath tube 10 to be 0.5 mm to 1.5 mm and more suitably to be 0.8 mm to 1.0 mm. Also, it is preferable for the thickness of the outside tube to be around 0.05 mm to 0.2 mm.

The inside tube 11 can be a synthetic resin tube composed of a fluorocarbon resin of PTFE, ETFE or the like; or composed of a light transparent resin of polyimide, polyester (for example, polyethylene terephthalate, polybutylene terephthalate), polyolefin (for example, polyethylene, polypropylene), polyamide, polyimide or the like.

As a synthetic resin used for the outside tube 12, it is possible to use, for example, polyolefin (for example, polyethylene, polypropylene), polyolefin elastomer (for example, elastomer or the like using polyethylene elastomer, polypropylene elastomer, ethylene-propylene copolymer or the like), polyvinyl chloride, ethylene-vinyl acetate copolymer, polyamide elastomer, polyurethane, a thermoplastic resin of fluorocarbon resin or the like, a silicone rubber and the like, and preferably, there is used polyethylene, polyamide elastomer or polyurethane. Also, it is preferable for the outside tube 12 to be flexible to such a degree as not to disturb the bending of the inner tube.

The intermediate tube 13 is a tube body having a lumen which passes-through from the proximal end to the distal end of the intermediate tube 13. It is preferable that the material forming the intermediate tube 13 is harder than the material forming the inside tube 11 and the outside tube 12. It is possible for the intermediate tube 13 to be a metal tube, a hard synthetic resin tube or the like. In the case of the metal tube, it is preferable to employ a tube body of stainless steel (SUS304, SUS316 or the like), a superelastic metal or the like, though it is not limited only to those materials. Also, for the hard synthetic resin tube, a tube composed of a fluorocarbon resin such as a fluorine resin of PTFE, ETFE or the like, polyimide, polyester (for example, polyethylene terephthalate, polybutylene terephthalate), polyolefin (for example, polyethylene, polypropylene), polyamide, polyimide and the like is preferably used, though is not limited only by those materials. It is preferable for the thickness of the intermediate tube to be around 0.05 mm to 0.2 mm.

Figure 7:
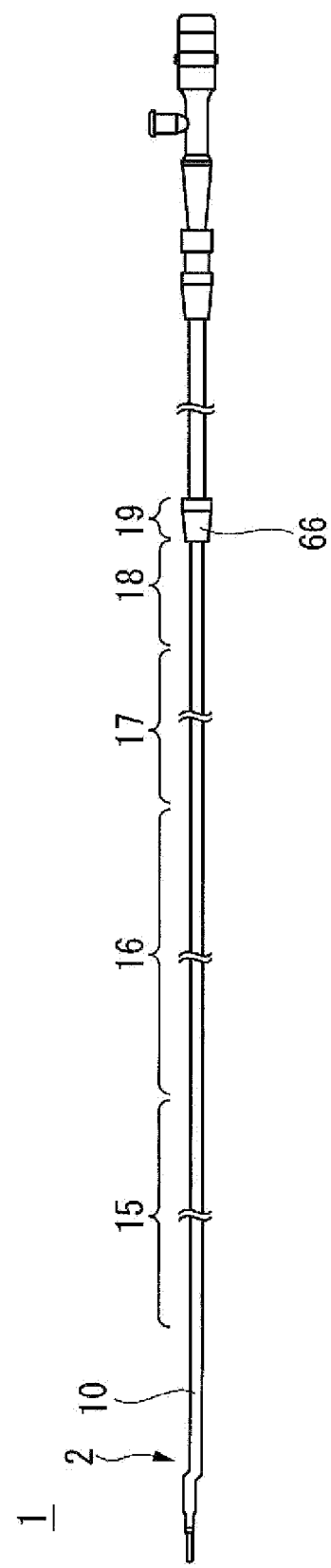
FIG. 7 is a plan view of an ultra-sound catheter.
Figure 8:
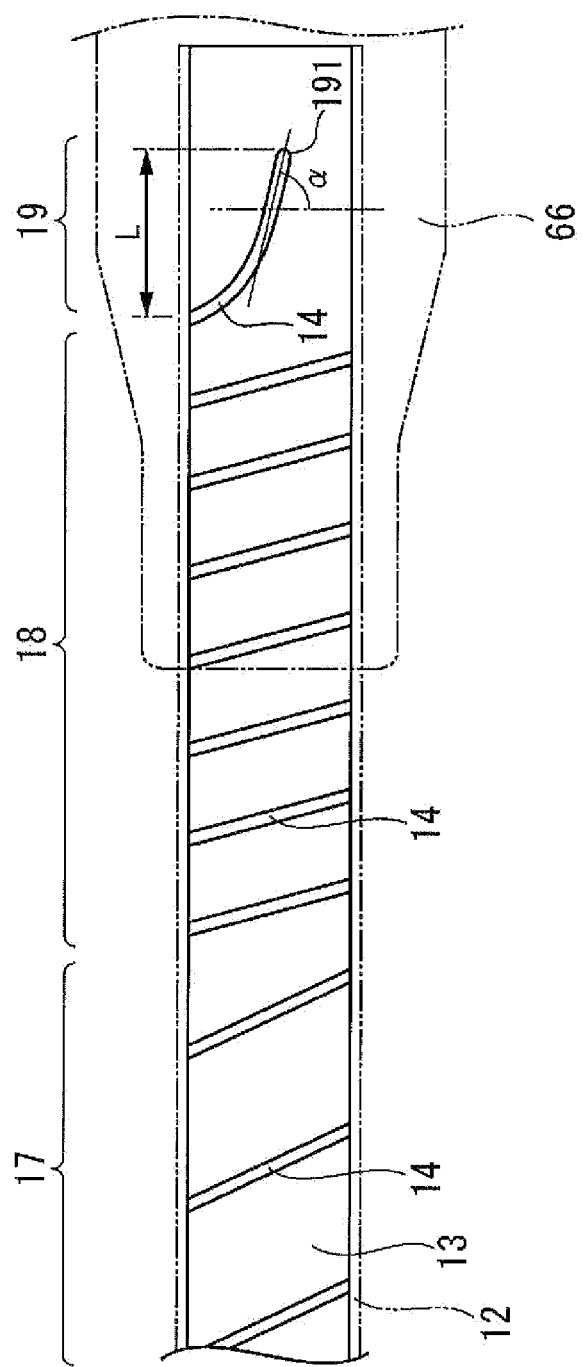
FIG. 8 is a plan view of a proximal portion of a sheath main body.

The intermediate tube 13 includes a spiral slit 14 which is continuous from the distal portion of the intermediate tube 13 toward the proximal portion of the intermediate tube 13. In the preferred embodiment, the distal-most end of the spiral slit 14 opens to the distal-most end of the intermediate tube 13, while the proximal-most end of the spiral slit 14 is spaced distally from the proximal-most end of the intermediate tube 13. In the illustrated embodiment, the spiral slit is a through slit, meaning the slit passes or extends radially completely through the intermediate tube 13 and communicates the inner and outer surfaces of the intermediate tube. The spiral slit 14 includes, as shown in FIGS. 6 to 8, a distal slit portion 15 whose slit density is the highest; a first intermediate slit portion 16 which is continuous with the distal slit portion 15 (immediately adjoins the distal slit portion 15) and also whose slit density is lower than that of the distal slit portion 15; a second intermediate slit portion 17 which is continuous with the first intermediate slit portion 16 (immediately adjoins the first intermediate slit portion 16) and also whose slit density is lower than that of the first intermediate slit portion 16; a proximal slit portion 18 which is continuous with the second intermediate slit portion 17 (immediately adjoins the second intermediate slit portion 17) and also whose slit density is higher than that of the second intermediate slit portion 17; and a slit termination portion 19 at which exists the termination end 191 on the proximal side of the slit. That is, the slit termination portion is the end of the slit on the proximal end. Slit density here means a total surface area of the slit portions which exist in a predetermined unit length in the axial direction of the intermediate tube 13. It is preferable for the slit intermediate portion to include the first intermediate slit portion 16 and the second intermediate sit portion 17, but it is also possible to provide only one slit intermediate portion. The spiral slit 14 can be formed by a laser process.

As depicted in FIG. 6, the slit 14 extends completely circumferentially around the intermediate tube 13 a plurality of times in each of the portions 15, 16, 17, 18.

The portion of the intermediate tube 13 between axially adjacent portions of the spiral slit 14 constitutes a spiral non-slitted portion of the tube 13. The non-slitted portion of the tube 13 in the distal slit portion 15 possesses a width (i.e., dimension along the axial extent of the tube) which is smaller than the width of the non-slitted portion of the tube 13 in the first intermediate slit portion 16, the non-slitted portion of the tube 13 in the first intermediate slit portion 16 possesses a width which is smaller than the width of the non-slitted portion of the tube 13 in the second intermediate slit portion 17, and the non-slitted portion of the tube 13 in the second intermediate slit portion 17 possesses a width which is larger than the width of the non-slitted portion of the tube 13 in the proximal slit portion 18. The intermediate tube 13 with the slit 14 is not a helically wound coil.

The slit density of the proximal slit portion 18 is preferably around 5/4 to 5/2 times of the slit density of the second intermediate slit portion 17 and it is preferable for the length of the proximal slit portion to be around 20 mm to 100 mm.

In the sheath tube 10 shown in FIG. 6, the slit density of the intermediate tube 13 is adjusted depending on the slit pitch (axial distance between immediately adjacent slits), preferably so that the longer the slit pitch, the lower the slit density. Specifically, in the intermediate tube 13, the slit pitch of the distal slit portion 15 is the shortest, the first intermediate slit portion 16 has a longer slit pitch than that of the slit distal portion 15, and the second intermediate slit portion 17 has a still longer slit pitch than that of the first intermediate slit portion 16. The proximal slit portion 18 preferably possesses a shorter slit pitch than that of the second intermediate slit portion 17. Consequently, the sheath tube 10 is constructed so that the sheath tube exhibits rigidity characteristics which becomes gradually higher from the distal end toward the proximal side and concurrently, some amount of flexibility is obtained at the proximal portion of the sheath tube.

The slit pitch of the distal slit portion 15 is preferably around 0.3 mm to 1.0 mm, and the length of the distal slit portion 15 is preferably around 10 mm to 100 mm.

The slit pitch of the first intermediate slit portion 16 is preferably around 1.0 mm to 5.0 mm, the slit pitch of the first intermediate slit portion 16 is preferably around 2 to 4 times the slit pitch of the distal slit portion 15, and the length of the first intermediate slit portion 16 is preferably around 50 mm to 250 mm.

The slit pitch of the second intermediate slit portion 17 is preferably around 3 mm to 6 mm, the slit pitch of the second intermediate slit portion 17 is preferably around 5/4 to 5/2 times the slit pitch of the proximal slit portion 18, and the slit pitch of the second intermediate slit portion 17 is preferably around 2 to 4 times the slit pitch of the first intermediate slit portion 16. The length of the second intermediate slit portion 17 is preferably around 500 mm to 900 mm.

The slit pitch of the proximal slit portion 18 is preferably around 2 mm to 4 mm, and the slit pitch of the proximal slit portion 18 is preferably around 2/5 to 4/5 times the slit pitch of the second intermediate slit portion 17.

Each of the distal slit portion 15, the first intermediate slit portion 16, the second intermediate slit portion 17 and the proximal slit portion 18 in this exemplified embodiment includes an extended portion having the same pitch for a predetermined length, but it is also possible for such portions to have a portion whose slit pitch changes gradually.

The intermediate tube 13 preferably includes a slit density transition portion of a predetermined length in which the slit density becomes higher gradually toward the proximal direction between the second intermediate slit portion 17 and the proximal slit portion 18 (specifically, the slit pitch becomes gradually shorter). Similarly, it is preferable for the intermediate tube 13 to include a slit density transition portion of a predetermined length in which the slit density becomes lower gradually toward the proximal direction between the distal slit portion 15 and the first intermediate slit portion 16 (specifically, the slit pitch becomes gradually longer). Similarly, it is preferable that the intermediate tube 13 includes a slit density transition portion of a predetermined length in which the slit density becomes gradually lower toward the proximal direction between the first intermediate slit portion 16 and the second intermediate slit portion 17 (specifically, the slit pitch becomes gradually longer).

In this exemplified embodiment, the outer diameter of the sheath tube 10 is 1 mm, the intermediate tube 13 is made of stainless steel, the slit pitch of the second intermediate slit portion 17 is 5 mm and the slit pitch of the proximal slit portion 18 is 3 mm. The length of the proximal slit portion 18 is 20 mm, and a slit density transition portion of 30 mm preferably exists between the second intermediate slit portion 17 and the proximal slit portion 18.

As shown in FIG. 8, the slit termination portion 19 is provided with the termination end 191 on the proximal most end of the spiral slit 14. The slit termination portion 19 is oriented at a slit inclination angle $\alpha$ representing the inclination angle of the slit termination portion 19 of the slit relative to the circumferential direction of the intermediate tube 13. The slit inclination angle $\alpha$ of the entire slit termination portion 19 of the slit is larger than the slit inclination angle $\alpha$ at the entire slit proximal portion 18. More specifically, the slit in the slit termination portion 19 extends in the axial direction of the sheath tube 10 more than the slit at the slit proximal portion 18. The slit termination portion 19 is a portion extending over relatively short region in the vicinity of the termination end 191 of the spiral slit 14 and it is not necessarily formed in a spiral shape by being wound around 360 degrees or more, though it is possible that it may sometimes be wound around 360 degrees or more. The axial direction length L of the slit termination portion 19 is preferably around 3 mm to 5 mm, and is 4 mm in this exemplified embodiment. The axial direction length L of the slit termination portion 19 is changeable in response to the conditions of the width of the slit, the slit inclination angle $\alpha$ and the like.

Figure 9:
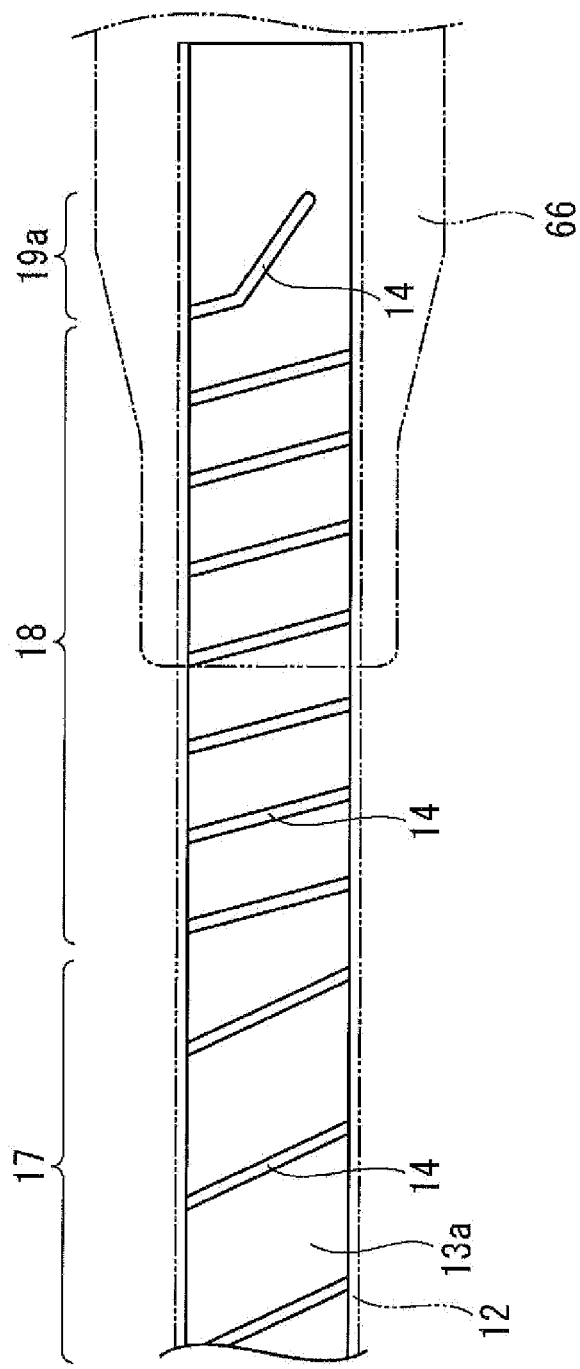
FIG. 9 is a plan view showing another example of the proximal portion of a sheath main body.

It is preferable for the slit inclination angle $\alpha$ to shift to become larger gradually between the slit proximal portion 18 and the slit termination portion 19. The slit termination portion 19 shown in FIG. 8 is constituted by a portion in which the slit inclination angle $\alpha$ changes gradually (i.e., the portion of the slit termination portion 19 closest to the slit proximal portion 18) and a portion of the termination end 191 side in which the slit inclination angle $\alpha$ is constant, but it is also possible for that portion to be constituted only by a portion whose slit inclination angle $\alpha$ changes gradually or, as shown in FIG. 9, it is also possible for that portion to be a slit termination portion 19a which is composed only of a portion whose slit inclination angle $\alpha$ is constant.

Also, at the slit termination portion 19, the slit inclination angle $\alpha$ is preferably 90 degrees or less. In this exemplified embodiment, the slit inclination angle $\alpha$ at the slit termination portion 19 is 80 degrees. It may sometimes happen that the slit inclination angle α exceeds 90 degrees.

Figure 10:
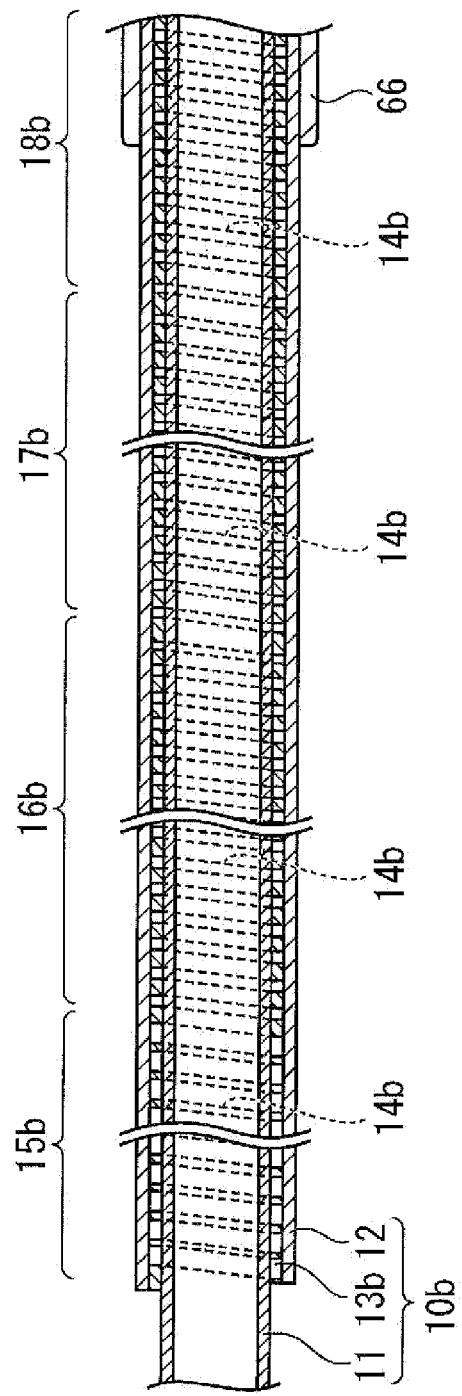
FIG. 10 is a plan view showing still another example of the sheath main body.

It is also possible for the slit density of the spiral slit 14 to be adjusted depending on the slit width such as in the sheath tube 10b of another example shown in FIG. 10. Here, the shorter the slit width is, the lower the slit density.

The intermediate tube 13b of this sheath tube 10b includes, in a manner similar to the intermediate tube 13 mentioned above, a spiral slit 14b which is continuous from the distal end to the proximal end. In this intermediate tube 13b, the slit width of a distal slit portion 15b is the widest, a first intermediate slit portion 16b possesses a slit width narrower than that of the distal slit portion 15b, and a second intermediate slit portion 17b has a slit width further narrower than that of the first intermediate slit portion 16b. Additionally, a proximal slit portion 18b possesses a slit width wider than that of the second intermediate slit portion 17b. Consequently, the sheath tube 10a is constituted such that the rigidity of the sheath tube 10a becomes gradually higher from the distal end toward the proximal side and concurrently, some amount of flexibility is obtained at the proximal portion.

The slit width of the distal slit portion 15b is around 0.08 mm to 0.12 mm, and the length of the distal slit portion 15b is around 10 mm to 100 mm.

Also, the slit width of the first intermediate slit portion 16b is around 0.07 mm to 0.1 mm, the slit width of the distal slit portion 15b is around 5/3 to 5/4 times of the slit width of the first intermediate slit portion 16b and the length of the first intermediate slit portion 16b is around 50 mm to 250 mm.

The slit width of the second intermediate slit portion 17b is around 0.06 mm to 0.09 mm, the slit width of the second intermediate slit portion 17b is around 9/10 to 6/7 times of the slit width of the first intermediate slit portion 16b and the length of the second intermediate slit portion 17b is around 500 mm to 900 mm.

The slit width of the proximal slit portion 18b is around 1.2 to 4 times the slit width of the second intermediate slit portion 17b, and the slit width of the proximal slit portion 18b is around 0.07 mm to 0.1 mm.

Each of the distal slit portion 15b, the first intermediate slit portion 16b, the second intermediate slit portion 17b, and the proximal slit portion 18b mentioned above to include a portion which is extended by maintaining the same width for a predetermined length. Here, it is also possible for each of the slit portions mentioned above to be a portion whose slit width changes gradually.

Then, it is preferable also for the intermediate tube 13b of this type to include the slit density transition portion of a predetermined length in which the slit width becomes gradually wider toward the proximal direction between the second intermediate slit portion 17b and the proximal slit portion 18b. Similarly, it is preferable for the intermediate tube 13b to include a slit density transition portion of a predetermined length in which the slit width becomes narrower gradually toward the proximal direction between the distal slit portion 15b and the first intermediate slit portion 16b. Similarly, the intermediate tube 13b preferably includes a slit density transition portion of a predetermined length in which the slit width becomes narrower gradually toward the proximal direction between the first intermediate slit portion 16b and the second intermediate slit portion 17b.

The slit termination portion 19 for the sheath tube 10b of the embodiment shown in FIG. 10 is similar to the slit termination portion 19 of the sheath tube 10 described above and shown in FIG. 8, and so a detailed explanation will not be repeated.

It is also possible for the slit density of the spiral slit 14 to be adjusted by changing both the length of the slit pitch and the slit width.

The proximal end of the sheath tube 10 is fixed by the anti-kink protector 65 (kink repression member). Specifically, the proximal portion of the sheath tube 10 is inserted into the lumen of the anti-kink protector 65 and is fixed in position in the lumen of the anti-kink protector 65.

The anti-kink protector 65 fixes the proximal portion of the sheath tube 10 at which the proximal portion of the slit proximal portion 18 and the slit termination portion 19 are positioned. More specifically, the proximal slit portion 18 and the slit termination portion 19 are positioned inside the anti-kink protector 65 over a predetermined length. In this way, the proximal slit portion 18 and the slit termination portion 19 are covered by the anti-kink protector 65 and are not exposed. The anti-kink protector 65 includes a distal portion 66 for kink repression which is closely-attached to the outer surface of the sheath tube 10 and also which is shrunk in its diameter toward the distal side. It is preferable for the distal most end of the slit proximal portion 18 to be positioned on the distal side by an amount of 5 mm to 150 mm from the distal most end of the distal portion 66 for kink repression of the anti-kink protector 65. In particular, it is preferable for the distal most end of the slit proximal portion 18 to be positioned distally of the distal most end of the distal portion 66a by an amount of 10 mm to 100 mm. Here, it is also possible to provide still another tube for reinforcement between the sheath tube 10 and the anti-kink protector 66.

Figure 11:
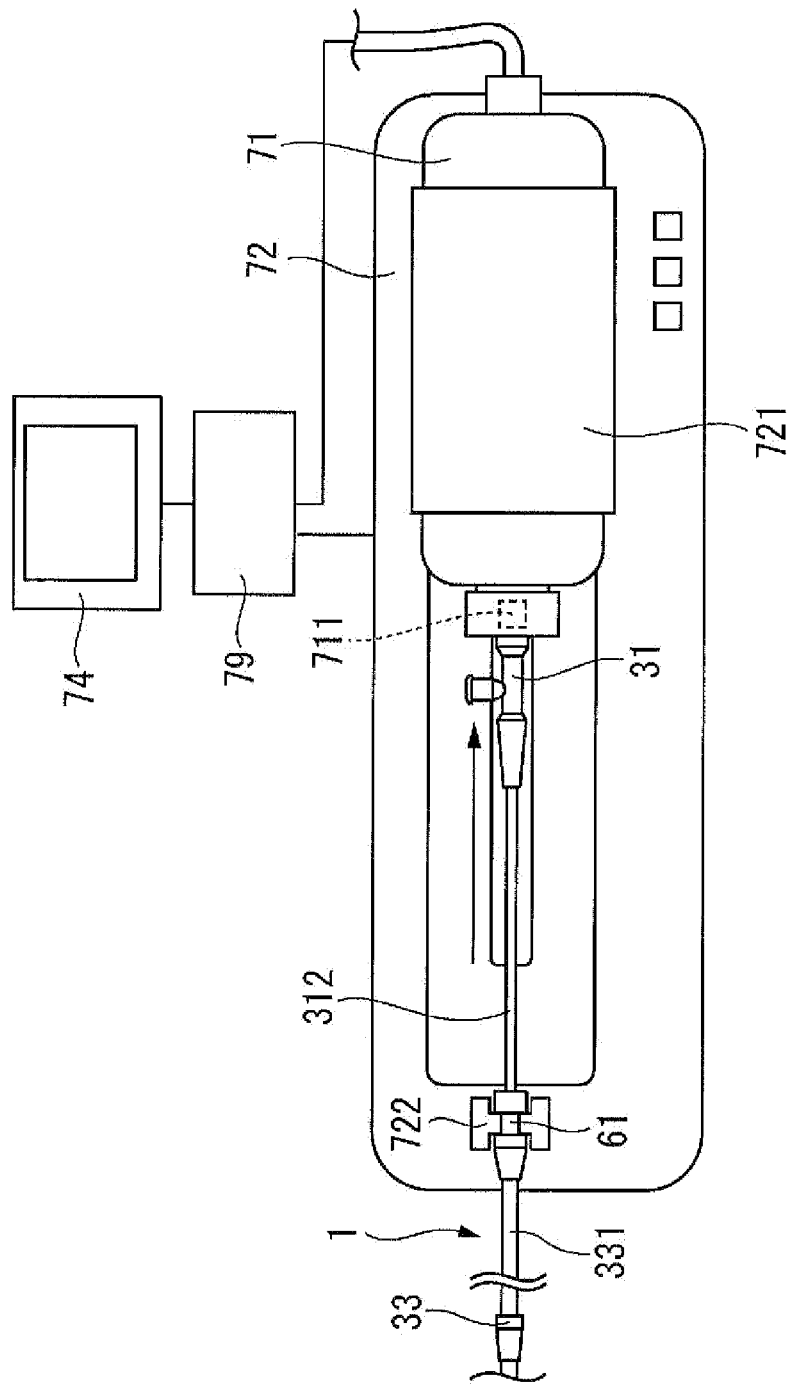
FIG. 11 is a plan view illustrating the pulling back of the ultra-sound catheter by an external drive apparatus.

The ultra-sound catheter 1 described above is connected to an external drive apparatus 7 shown in FIG. 11 and is driven by this external drive apparatus 7.

The external drive apparatus 7 includes a scanner device 71 installed with an external drive power supply of a motor or the like, an axial direction moving device 72 which grabs the scanner device 71 and which causes the axial direction movement depending on the motor and the like, a control unit 79 for controlling the scanner device 71 and the axial direction moving device 72, and a display unit 74 for displaying an image obtained by the transducer unit 41.

The axial direction moving device 72 includes a scanner device grab portion 721 for grabbing and fixing the scanner device 71, and a sheath support portion 722 for supporting the sheath 2 so as not to be deviated at the time of the pulling-back thereof.

The scanner device 71 includes a female connector 711 to which the male connector 51 of the ultra-sound catheter 1 is connectable and depending on the aforesaid connection, the transmission and reception of the signal with respect to the transducer unit 41 will become possible and simultaneously, it becomes possible to rotate the drive shaft 42.

The ultra-sound scan (SCAN) in the ultra-sound catheter 1 is carried out, depending on a mechanism of scanning the light which is transmitted and received by the ultrasonic transducer 411 provided in the housing 412, in approximately the radial direction by transmitting a rotational motion of the motor in the scanner device 71 to the drive shaft 42 and by rotating the housing 412 fixed at the distal end of the drive shaft 42. By pulling the whole ultra-sound catheter 1 toward the hand-side and by causing the ultrasonic transducer 411 to move in the longitudinal direction, it is possible to obtain a cross-sectional image of 360° until any desired position by a scanning manner in the surrounding tissues extending over the axial direction inside the blood vessel.

Set forth below is a description of the method of using the disclosed ultra-sound catheter 1. Before inserting the sheath 2 of the ultra-sound catheter 1 into a body cavity or lumen (e.g., blood vessel), a priming operation is performed for filling the inside of aforesaid ultra-sound catheter 1 with a physiological salt solution. By carrying out the priming operation, the air in the ultra-sound catheter 1 is removed and there is prevented a phenomenon in which air enters into the lumen of the blood vessel or the like.

In order to carry out the priming, first the physiological salt solution is injected into the port 311 of the hub 31 while pulling the hub 31 maximally toward the hand-side of the user, that is in a state in which the inner tube 312 is pulled maximally from the outer tube 331 (see FIG. 3). The injected physiological salt solution is to be filled sequentially from the hub 31 into the inside of the sheath 2. When the inside of the ultra-sound catheter 1 is filled completely with the physiological salt solution, the physiological salt solution is removed from the priming lumen 231 which is formed in the filling liquid in/out-path member 23 of the sheath 2 (see FIG. 2). Thus, the filling of the physiological salt solution can be confirmed.

Next, the hub 31 is pressed and there is obtained a state in which the inner tube 312 is inserted maximally in the outer tube 331 (see FIG. 1). In this state, the sheath 2 is to be inserted into the inside of the body and then, the insertion thereof is stopped after the distal end of the sheath 2 exceeds the target lesion.

Next, the male connector 51 of the ultra-sound catheter 1 (see FIG. 4) is connected to the female connector 711 of the external drive apparatus 7 shown in FIG. 11, and the unit connector main body 61 is interlinked to the sheath support portion 722 of the external drive apparatus 7 so that the unit connector main body 61 is generally sandwiched by the sheath support portion 722.

Next, the axial direction moving device 72 is operated, the ultrasonic transducer 411 moves toward the axial direction while pulling the hub 31 toward the hand-side, and the region extending over the forward and backward portions of the target lesion is observed by the ultrasonic transducer 411 through the acoustic window portion of the heath tube 10.

When the measurement is completed, the axial direction moving device 72 and the scanner device 71 are deactivated.

In the ultra-sound catheter 1 disclosed here, the intermediate tube 13 provided in the sheath 2 applies rigidity to the sheath 2 and concurrently, the slit density is higher in the direction from the slit intermediate portion 16 to the slit distal portion 15, so that it is possible to provide flexibility on the distal side and rigidity on the proximal side. It is thus possible to satisfactorily accomplish the insertion of the catheter into a living body in a relatively easier manner. Further, the intermediate tube 13 is provided with the proximal portion 18 which is continuous with (immediately adjoins) the slit intermediate portion 17 and whose slit density is higher than that of the slit intermediate portion 17. A proximal portion is thus provided having a certain degree of flexibility. At the same time, satisfactory steerability is provided at the proximal portion of the sheath 2 and, at the same time, suppression of the occurrence of kinking at the proximal portion is achieved. In particular, the proximal portion of the sheath 2 is interlinked with the steering unit 3, and it may be assumed that kinking which will arise will occur in the vicinity of the interlink portion. But it is possible to repress or suppress the occurrence of kinking by providing, as a part of the features forming the catheter construction, the slit proximal portion 18 described above.

The slit termination portion 19 whose slit inclination angle α is larger than that of the slit proximal portion 18 is formed on the proximal side of the slit proximal portion 18. It is thus possible, for example, to repress, inhibit or prevent the occurrence of a crack at the termination end 191 of the spiral slit 14 when a tensile force or a bending moment is applied along the axial direction of the sheath 2. More specifically, to suppress the occurrence of kinking at the proximal portion of the sheath 2, there is provided the slit proximal portion 18 whose slit density is higher than that of the slit intermediate portion 17, but if the slit termination portion 19 is not provided, the stress will be concentrated at the termination end of the slit.

On the other hand, the ultra-sound catheter 1 disclosed here includes the slit termination portion 19 whose slit inclination angle α is larger than that of the slit proximal portion 18 on the proximal side of the slit proximal portion 18. If the slit inclination angle α is relatively large, the stress acting at the termination end 191 does not become excessive also when a tensile force or a bending moment acts on, or is applied to, the sheath 2. It is thus possible to suppress, inhibit or prevent the occurrence of a crack at the termination end 191 and to improve security. Consequently, the catheter construction is not so susceptible to the occurrence of a crack at the termination end 191, thus improving security, and is also not so susceptible to the occurrence of kinking at the proximal portion of the sheath 2.

Also, the slit inclination angle α of the slit termination portion 19 changes so as to become gradually larger in the proximal direction from the slit proximal portion 18. The rigidity of the slit intermediate portion 17 thus changes relatively smoothly. Concurrently, stress concentration is suppressed and workability and security are improved.

In a case in which the slit inclination angle α is 90 degrees, when a tensile force or a bending moment acts on, or is applied to the sheath 2, a force hardly acts in the direction of opening the slit. Consequently, to suppress the occurrence of the crack at the termination end 191, it is preferable for the slit inclination angle α of the slit termination portion 19 to be larger than the slit inclination angle α at the slit proximal portion 18 and to be 90 degrees or less. As illustrated, axially adjacent slits 14 in the proximal slit portion 18 are parallel to each other, and the slit 14 in the slit termination portion 19 deviates from this parallel arrangement (i.e., the slit 14 in the slit termination portion 19 is not parallel to the axially adjacent slits 14 in the proximal slit portion 18). As also illustrated, the axis of the slit 14 in the slit termination portion 19 intersects or crosses the axes of the axially adjacent slits 14 in the proximal slit portion 18.

In a situation in which the slit inclination angle α is 90 degrees, a force hardly acts in the direction of opening the slit. Even if it the slit 14 in the slit termination portion 19 is arranged so that the slit inclination angle α at the termination end 191 of the slit termination portion 19 is approximately 90 degrees, this arrangement is effective for repressing or inhibiting the occurrence of cracking at the termination end 191.

The description above describes the disclosed construction applied to an ultra-sound catheter, but it is possible to apply a similar construction to, for example, an optical probe for diagnostic apparatus (catheter) utilizing light such as an optical coherent tomography diagnostic apparatus, an optical frequency domain imaging apparatus and the like, and a balloon catheter. It is thus possible to apply the construction disclosed here to every catheter if a tube body is included as a part of the catheter.

In addition, in the case of another example shown in FIG. 12, it is also possible for the termination end 191c of the slit in the slit termination portion 19c to be formed as a hole whose diameter is larger than the width of the slit. This hole helps further suppress the stress concentration in the termination end 191c while also more reliably inhibiting or suppressing the occurrence of a crack.

The detailed description above describes features and aspects of embodiments of a catheter (ultra-sound catheter). The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A catheter comprising:
    a sheath possessing a size allowing the sheath to be inserted into a living body;
    the sheath comprising an inside tube, an intermediate tube and an outside tube;
    the inside tube, the intermediate tube and the outside tube being coaxially arranged and each possessing a lumen open at opposite end portions of the respective tube;
    the inside tube, the intermediate tube and the outside tube each possessing an inner surface and an outer surface, the inner surface of the outer tube being in contact with an outer surface of the intermediate tube, and the inner surface of the intermediate tube being in contact with the outer surface of the inner tube;
    the intermediate tube including a spiral slit extending continuously from a distal side of the intermediate tube to a proximal side of the intermediate tube, the slit extending radially completely through the intermediate tube to communicate the inner surface of the intermediate tube with the outer surface of the intermediate tube;
    the intermediate tube comprising a first slit portion in which the slit is located, a second slit portion in which the slit is located and a third slit portion in which the slit is located, the slit in the first slit portion possessing a slit density greater than the slit density of the slit in the second slit portion, and the slit in the third slit portion possessing a slit density greater than the slit density of the slit in the second portion, the second slit portion being positioned axially between the first slit portion and the third slit portion, the first slit portion being positioned distally of the third slit portion, and the first slit portion and the third slit portion possessing different slit densities, a proximal end portion of the third slit portion including a plurality of axially adjacent slits that are parallel to one another;
    the intermediate tube comprising a slit termination portion in which is located a terminating portion of the slit at a proximal end portion of the slit, the slit termination portion being positioned proximally of the third slit portion, the slit termination portion continuing immediately from a proximal-most end of the third slit portion, the spiral slit possessing a termination end at which a proximal-most end of the slit terminates, the termination end being located in the slit termination portion of the intermediate tube; and
    the slit in the slit termination portion and the slit in the third slit portion extending at an inclination angle relative to a circumferential direction of the intermediate tube, the slit in the slit termination portion deviates from an imaginary continuation of a proximal-most end portion of the third slit portion so that the inclination angle of the slit in the slit termination portion being is larger than the inclination angle of the slit in the third slit portion to thereby reduce occurrence of a crack at the termination end.

2. The catheter according to claim 1, wherein the inclination angle of the slit termination portion changes gradually from the slit proximal portion.

3. The catheter according to claim 1, wherein the inclination angle of the slit termination portion is 90 degrees or less.

4. The catheter according to claim 1, wherein the second slit portion is a second intermediate slit portion located proximally of a first intermediate slit portion, the first intermediate slit portion being located distally of the second intermediate slit portion, the slit in the first intermediate slit portion possessing a slit density greater than the slit density of the slit in the second intermediate slit portion.

5. The catheter according to claim 4, further comprising a through hole at the proximal-most end of the slit, the through hole possessing a diameter greater than a width of the slit in the slit termination portion.

6. The catheter according to claim 4, further comprising a kink repression member covering the slit in the slit termination portion, the kink repression member possessing an outer diameter which becomes gradually smaller in a distal direction.

7. A catheter comprising:
    a sheath possessing a size allowing the sheath to be inserted into a living body;
    the sheath comprising two coaxial tubes each of which possesses a lumen open at opposite end portions of the respective tube, each tube possessing an inner surface and an outer surface, the inner surface of one of the tubes being in contact with an outer surface of the other tube, the two tubes comprising a first tube and a second tube;
    the first tube including a spiral slit extending continuously from a distal side of the first tube to a proximal side of the first tube, the slit extending completely radially through first tube;
    the first tube including plural slit portions in which the slit is located, the slit in each slit portion extending completely around a circumference of the first tube plural times;
    one of the plural slit portions possessing a slit density different from the slit density of the slit in another of the slit portions, the other slit portion being positioned proximally of the one slit portion, a proximal end portion of the other slit portion including a plurality of axially adjacent slits that are parallel to one another;
    the first tube comprising a slit termination portion in which a proximal end portion of the spiral slit is located, the slit terminating at a terminating end located in the slit termination portion of the first tube, the slit termination portion being positioned proximally of the other slit portion, the slit termination portion continuing immediately from a proximal-most end of the other slit portion; and
    the slit in the slit termination portion and the slit in the other slit portion extending at an inclination angle relative to a circumferential direction of the intermediate tube, the slit in the slit termination portion not being parallel to the axially adjacent slits in the proximal end portion of the other slit portion, and the inclination angle of the slit in the slit termination portion is larger than the inclination angle of the slit in the other slit portion to thereby reduce occurrence of a crack at the terminating end.

8. The catheter according to claim 7, wherein the inclination angle of the slit in the slit termination portion changes gradually from the slit in the other slit portion.

9. The catheter according to claim 7, the one slit portion is a distal slit portion and the other slit portion is a proximal slit portion, and wherein the first tube also comprises first and second intermediate slit portions in which the slit is located, the slit density of the slit in the first intermediate slit portion being different from the slit density of the slit in the second intermediate slit portion.

10. The catheter according to claim 9, wherein the first intermediate slit portion is located distally of the second intermediate slit portion.

11. The catheter according to claim 10, wherein the slit density of the slit in the first intermediate slit portion is greater than the slit density of the slit in the second intermediate slit portion.

12. The catheter according to claim 11, further comprising a kink repression member covering the slit in the slit termination portion, the kink repression member possessing an outer diameter which becomes gradually smaller in a distal direction.

13. The catheter according to claim 7, further comprising a through hole at a proximal-most end of the slit, the through hole possessing a diameter greater than a width of the slit in the slit termination portion.

14. The catheter according to claim 7, further comprising a kink repression member covering the slit in the slit termination portion, the kink repression member possessing an outer diameter which becomes gradually smaller in a distal direction.

15. A catheter comprising:
   a sheath possessing a size which is insertable into a living body;
   the sheath including a tubular reinforcement layer comprised of at least one layer;
   the tubular reinforcement layer including a spiral slit extending continuously from a distal side of the tubular reinforcement layer to a proximal side of the tubular reinforcement layer;
   a termination end of the spiral slit is located at a proximal side of a proximal slit portion of the tubular reinforcement layer, the slit being located in the proximal slit portion of the tubular reinforcement layer;
   the tubular reinforcement layer also comprising a slit termination portion in which a proximal portion of the slit, including the termination end, is located;
   a proximal end portion of the proximal slit portion including a plurality of axially adjacent slits that are parallel to one another, the slit termination portion continuing immediately from a proximal-most end of the proximal slit portion;
   the slit in the slit termination portion and the slit in the proximal slit portion extending at an inclination angle relative to a circumferential direction of the intermediate tube, a proximal portion of the slit in the slit termination portion possessing an axis, the axis of the proximal portion of the slit in the slit termination portion intersecting the axially adjacent slits in the proximal end portion of the other slit portion as seen from a side of the catheter so that the inclination angle of the slit in the slit termination portion being larger than the inclination angle of the slit in the proximal slit portion to thereby reduce occurrence of a crack at the termination end.

16. The catheter according to claim 15, wherein the slit termination portion is a portion in which the inclination angle of the slit changes gradually from the proximal slit portion.

17. The catheter according to claim 15, wherein the inclination angle of the slit in the slit termination portion is 90 degree or less.

18. The catheter according to claim 15, wherein the tubular reinforcement layer includes an intermediate slit portion distal of the proximal slit portion, the slit in the intermediate slit portion possessing a slit density less than the slit density of the slit in the slit proximal portion, the tubular reinforcement layer also including a slit distal portion, the slit in the slit distal portion possessing a slit density greater than the slit density of the slit in the intermediate slit portion.

19. The catheter according to claim 18, further comprising a kink repression member covering the slit in the slit termination portion, the kink repression member possessing an outer diameter which becomes gradually smaller in a distal direction.

20. The catheter according to claim 15, further comprising a kink repression member covering the slit in the slit termination portion, the kink repression member possessing an outer diameter which becomes gradually smaller in a distal direction.

* * * * *